(12) United States Patent
McLendon et al.

(10) Patent No.: US 10,473,955 B2
(45) Date of Patent: Nov. 12, 2019

(54) AUTOMATED DIGITAL MIGRAINE DIARY

(71) Applicant: SensorRx, Inc., Houston, TX (US)

(72) Inventors: George McLendon, Davidson, NC (US); Alex Dzeda, Houston, TX (US); Senthil Natarajan, Houston, TX (US)

(*) Notice: Subject to any disclaimer, the term of this patent is extended or adjusted under 35 U.S.C. 154(b) by 25 days.

(21) Appl. No.: 15/343,503

(22) Filed: Nov. 4, 2016

(65) Prior Publication Data

US 2017/0139233 A1    May 18, 2017

Related U.S. Application Data

(60) Provisional application No. 62/254,827, filed on Nov. 13, 2015.

(51) Int. Cl.

| | | |
|---|---|---|
| *G02C 7/10* | (2006.01) | |
| *A61B 5/1455* | (2006.01) | |
| *A61B 5/00* | (2006.01) | |
| *A61N 5/06* | (2006.01) | |
| *G16H 40/67* | (2018.01) | |
| *G16H 50/20* | (2018.01) | |
| *A61B 5/024* | (2006.01) | |
| *A61B 5/053* | (2006.01) | |
| *A61B 5/11* | (2006.01) | |
| *A61B 5/0402* | (2006.01) | |
| *A61B 5/16* | (2006.01) | |

(52) U.S. Cl.
CPC .......... *G02C 7/101* (2013.01); *A61B 5/14552* (2013.01); *A61B 5/4824* (2013.01); *G02C 7/104* (2013.01); *A61B 5/024* (2013.01); *A61B 5/0533* (2013.01); *A61B 5/1118* (2013.01); *A61B 5/681* (2013.01); *A61B 5/6898* (2013.01); *A61B 2560/0242* (2013.01)

(58) Field of Classification Search
CPC ........ G02C 7/101; G02C 7/104; A61B 5/024; A61B 5/0533; A61B 5/1118; A61B 5/14552; A61B 5/4824; A61B 5/681; A61B 5/6898; A61B 2560/0242
USPC ....................................... 351/159.6, 200–246
See application file for complete search history.

(56) References Cited

U.S. PATENT DOCUMENTS

| | | | |
|---|---|---|---|
| 7,874,666 B2 | 1/2011 | Xu et al. | |
| 2003/0144829 A1* | 7/2003 | Geatz ................. | G06F 19/3418 703/22 |
| 2014/0327967 A1* | 11/2014 | Blair .................... | A61N 5/0618 359/589 |
| 2017/0116379 A1* | 4/2017 | Scott ....................... | G06F 19/28 |
| 2017/0231490 A1* | 8/2017 | Toth ....................... | A61B 3/113 600/558 |

OTHER PUBLICATIONS

Caddy. Here's how your phone is tracking you right now. Techradar. Available at http://www.techradar.com/news/phone-and-communications/mobile-phones/sensory-overload-how-your-smartphone-is-becoming-part-of-you-1210244 (10 pgs) (Apr. 9, 2016).

(Continued)

*Primary Examiner* — Collin X Beatty
(74) *Attorney, Agent, or Firm* — John L. Sotomayor

(57) ABSTRACT

Disclosed herein are platforms and methods for collecting migraine associated data. Migraine associated data is collected automatically, such as via a sensor, or is self-reported manually.

18 Claims, 2 Drawing Sheets

(56) References Cited

OTHER PUBLICATIONS

Ma et al. Smart sunglasses based on electrochromic polymers. Polym Eng Sci 48:2224-2228 (2008).
Osterholm et al. Four Shades of Brown: Tuning of Electrochromic Polymer Blends Toward High-Contrast Eyewear. ACS Appl Mater Interfaces 7(3):1413-1421 (2015).
Xu et al. Switchable window based on electrochromic polymers. J Mater Res 19(7):2072-2080 (2004).

* cited by examiner

AUTOMATED DIGITAL MIGRAINE DIARY

CROSS-REFERENCE

This application claims the benefit of U.S. Provisional Application No. 62/254,827, filed Nov. 13, 2015, which is incorporated herein by reference in its entirety.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

SUMMARY OF THE INVENTION

Figure 1:
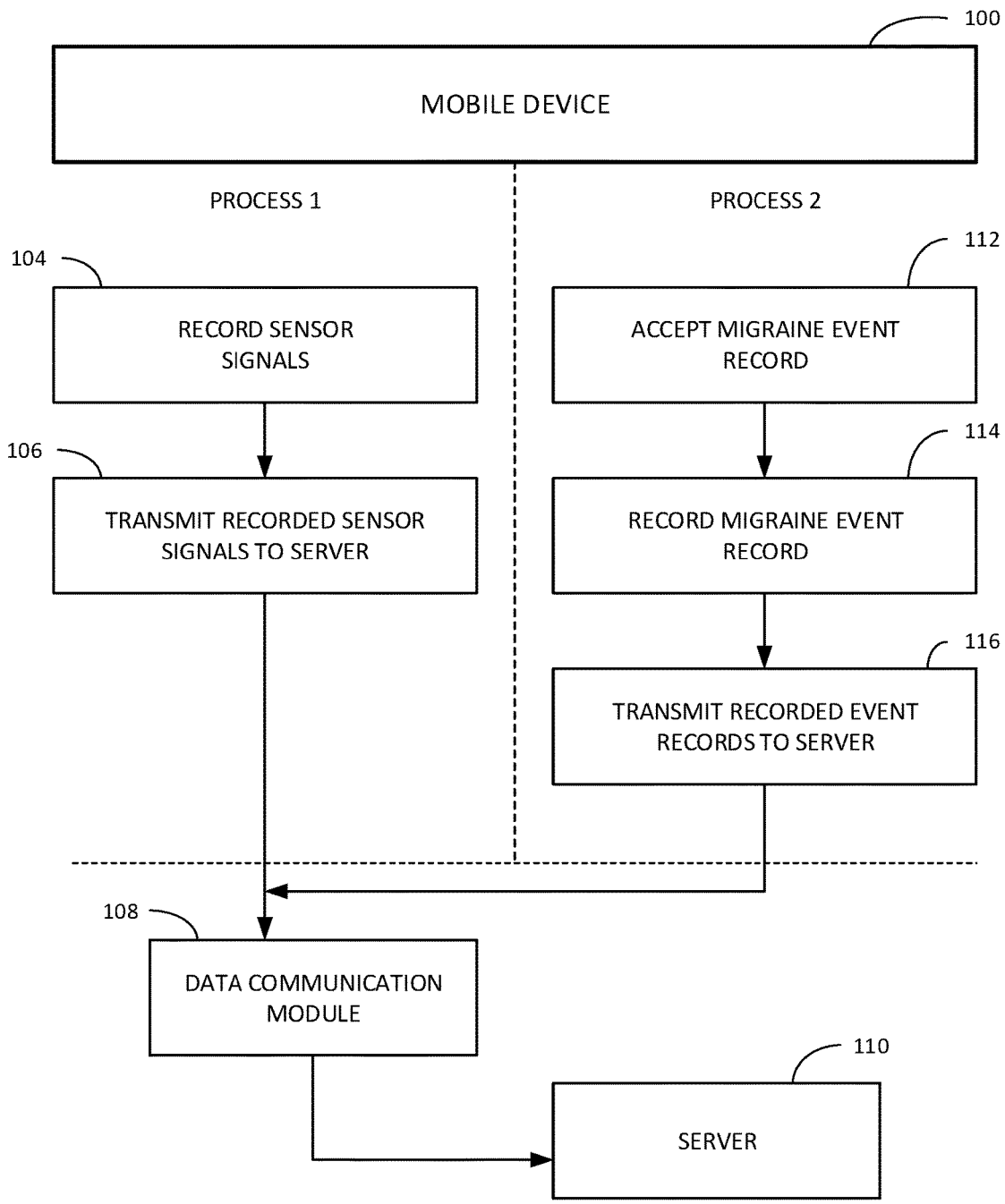
FIG. 1 is a process flow diagram for mobile device processes for capturing, recording, and transmitting sensor and event record data consistent with certain embodiments of the present invention.

Disclosed herein, in certain embodiments, is a platform for collecting migraine associated data for an individual who experiences migraines, comprising: a sensor comprising: a detector used to collect migraine associated data; and a communications element used to transmit migraine associated data collected by the detector to non-transitory computer readable storage media; and a non-transitory computer readable storage media encoded with a computer program including instructions executable by a processor to create an application comprising: a software module used to receive the migraine associated data from the sensor; and a software module used to present an interface allowing the user to interact with the migraine associated data. In some embodiments, the platform further comprising an ocular device for reducing occurrence, duration, or severity of migraine headaches in the individual in need thereof, operatively connected to the non-transitory computer readable storage media and the sensor, comprising: a first mode that allows a target light wavelength or a target light intensity to pass through the first lens; a second mode that reduces or substantially blocks the target light wavelength or the target light intensity from passing through the first lens; a voltage source operatively coupled to the first lens and configured to generate a voltage, wherein application of the voltage to the first lens switches the first lens from the first mode to the second mode; and an activator operatively coupled to the voltage source, and configured to activate the voltage source upon receipt of a signal from a signal receiver; wherein the target light wavelength or the target light intensity is associated with an occurrence of migraine headaches in the individual. In some embodiments, the sensor is physically coupled to the ocular device. In some embodiments, the platform comprises a plurality of sensors. In some embodiments, the migraine associated data comprises environmental data. In some embodiments, the environmental data is selected from the group consisting of: light, sound, temperature, air quality, humidity, barometric pressure, altitude, and location data. In some embodiments, the migraine associated data comprises physiological data. In some embodiments, the physiological data is selected from the group consisting of: heart, activity, sleep, oxygen saturation of the blood, and electrodermal activity data. In some embodiments, the migraine associated data comprises self-reported data. In some embodiments, the self-reported data is selected from the group consisting of: sleep, activity, diet, medication, supplement, menstruation status, emotional state, pain, migraine location, biomarker, and water intake data. In some embodiments, the sensor records a baseline measurement of the migraine associated data. In some embodiments, the baseline measurement of the migraine associated data is recorded one, two, three, four, five, six, seven, eight, nine, ten, twelve, twenty four, or forty eight times per day. In some embodiments, the baseline measurement of the migraine associated data is recorded at an interval specified by the individual. In some embodiments, the sensor is located in a mobile device. In some embodiments, the sensor is located in a smart phone or smart watch. In some embodiments, the sensor is located in a wearable device. In some embodiments, the measurement of migraine associated data is taken when the sensor is triggered automatically. In some embodiments, the measurement of migraine associated data is taken when the sensor is triggered manually.

Disclosed herein, in certain embodiments, is a method of recording migraine associated data for an individual who experiences migraines comprising the steps of: receiving a sensor operatively connected to a non-transitory computer readable storage media; and instructing of the non-transitory computer readable storage media to signal the sensor to make a measurement of the migraine associated data, wherein making a measurement of the migraine associated data comprises: recording of the migraine associated data by the sensor; transmitting the migraine associated data from the sensor to the non-transitory computer readable storage media; and storing the migraine associated data on a memory of the non-transitory computer readable storage media. In some embodiments, the method further comprises receiving an ocular device for reducing occurrence, duration, or severity of migraine headaches in the individual in need thereof, operatively connected to the non-transitory computer readable storage media and the sensor, comprising: a first mode that allows a target light wavelength or a target light intensity to pass through the first lens; a second mode that reduces or substantially blocks the target light wavelength or the target light intensity from passing through the first lens; a voltage source operatively coupled to the first lens and configured to generate a voltage, wherein application of the voltage to the first lens switches the first lens from the first mode to the second mode; and an activator operatively coupled to the voltage source, and configured to activate the voltage source upon receipt of a signal from a signal receiver; wherein the target light wavelength or the target light intensity is associated with an occurrence of migraine headaches in the individual. In some embodiments, the sensor is physically coupled to the ocular device. In some embodiments, the instructing of the non-transitory computer readable storage media to signal the sensor is initiated manually. In some embodiments, instructing of the non-transitory computer readable storage media to signal the sensor is initiated automatically. In some embodiments, automatic initiation of the sensor is to record a baseline measurement of the migraine associated data. In some embodiments, the baseline measurement of the migraine associated data is recorded one, two, three, four, five, six, seven, eight, nine, ten, twelve, twenty four, or forty eight times per day. In some embodiments, the baseline measurement of the migraine associated data is recorded at an interval specified by the individual. In some embodiments, the migraine associated data comprises environmental data.

In some embodiments, the environmental data is selected from the group consisting of: light, sound, temperature, air quality, humidity, barometric pressure, altitude, and location data. In some embodiments, the migraine associated data comprises physiological data. In some embodiments, the physiological data is selected from the group consisting of: heart, activity, sleep data, oxygen saturation of the blood, and electrodermal activity. In some embodiments, the migraine associated data comprises self-reported data. In some embodiments, the self-reported data is selected from the group consisting of: sleep, activity, diet, medication, supplement, menstruation status, emotional state, pain, migraine location, biomarker, and water intake data. In some embodiments, the sensor is located in a mobile device. In some embodiments, the sensor is located in a smart phone or smart watch. In some embodiments, the sensor is located in a wearable device. In some embodiments, the measurement of migraine associated data is taken when the sensor is triggered automatically. In some embodiments, the measurement of migraine associated data is taken when the sensor is triggered manually. In some embodiments, the method further comprises generating a report of the migraine associated data. In some embodiments, the method further comprises transmitting the recorded migraine associated data from the memory of the non-transitory computer readable storage media to a server. In some embodiments, the migraine associated data from a plurality of individuals is aggregated on the server.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby Certain Definitions The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The term "sensor pad" refers to a device that, when engaged by the subject, communicates with the activator. In some embodiments, the sensor pad is a button, dial, switch, touch screen, or microphone. In some embodiments, a button is engaged by pressing on the button. In some embodiments, a dial is engaged by turning the dial. In some embodiments, the switch is engaged by pressing or toggling the switch. In some embodiments, a touch screen is a surface utilizing a touch detection technology. In some embodiments, the touch detection technology includes resistive, capacitive, infrared, surface acoustic wave, and near field imaging technologies.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

"Treating" or "treatment" of a state, disorder or condition (e.g., migraine) includes: (1) preventing or delaying the appearance of clinical or sub-clinical symptoms of the disorder developing in a human that is afflicted with or pre-disposed to the disorder but does not yet experience or display clinical or subclinical symptoms of the disorder; and/or (2) inhibiting the disorder, including arresting, reducing or delaying the clinical manifestation of the disorder or at least one clinical or sub-clinical symptom thereof; and/or (3) relieving the disorder, e.g., causing regression of the disorder or at least one of its clinical or sub-clinical symptoms; and/or (4) causing a decrease in the severity of one or more symptoms of the disorder. The benefit to a subject to be treated is either statistically significant or at least perceptible to the patient or to the physician.

Migraines

Migraine is a chronic, neurological disease characterized by recurrent moderate to severe headaches often in association with a number of autonomic nervous system symptoms. Migraines affect nearly one billion people worldwide, and are more common in women than men, at 19% and 11% affected, respectively. Examples of symptoms, by way of non-limiting examples, include nausea, vomiting, blurred vision, nasal stuffiness, diarrhea, frequent urination, pallor, sweating, and sensitivity to light, sound, or smell. Current prevention of migraines includes the use of medications, nutritional supplements, lifestyle alterations, and surgery.

Migraines are often triggered by environmental cues, such as changes in the weather, light, sound, air quality, and odors. Avoidance of these triggers, in addition to acute symptomatic control and pharmacological prevention, helps to manage migraines. Monitoring exposure to potential triggers can help an individual pinpoint triggers likely to contribute to development of a migraine. However, self-monitoring can result in misidentification of triggers through non-thorough recording of potential trigger exposure, misreporting of potential trigger exposure, or human bias in reporting or interpreting the data.

Platform

Disclosed herein, in certain embodiments, is a platform for collecting migraine associated data for an individual who experiences migraines comprising: (a) a sensor comprising: (i) a detector used to collect migraine associated data; and (ii) a communications element used to transmit migraine associated data collected by the detector to non-transitory computer-readable storage media; and (b) a non-transitory computer readable storage media encoded with a computer program including instructions executable by a processor to create an application comprising: a software module used to receive the migraine associated data from the sensor; and a software module used to present an interface allowing the user to interact with the migraine associated data.

Migraine Associated Data

In some embodiments, the migraine associated data comprises environmental data. In some embodiments, the environmental data is selected from the group consisting of: light, sound, temperature, air quality, humidity, barometric pressure, altitude, location data, or any combination thereof. In some embodiments, the migraine associated data comprises physiological data. In some embodiments the physiological data is selected from the group consisting of: heart, activity, sleep data, oxygen saturation of the blood, and electrodermal activity or any combination thereof. In some embodiments, the migraine associated data comprises self-reported data. In some embodiments the self-reported data is selected from the group consisting of diet, medication, vitamins, supplements, menstruation status, emotional state, pain intensity, migraine location, sleep, activity, biomarker, water intake, or any combination thereof. In some embodiments, the migraine associated data is recorded when the sensor is triggered automatically. In some embodiments, the measurement of migraine associated data is taken when the sensor is triggered manually. In some embodiments, the migraine associated data is taken as a baseline measurement. In some embodiments, the migraine associated data is taken instantaneously when the sensor is triggered. In some embodiments, the measure of migraine associated data is taken over a period of time after the sensor is triggered. In some embodiments, the baseline measure of migraine associated data is recorded one, two, three, four, five, six, seven, eight, nine, ten, twelve, twenty four, or forty eight times per day. In some embodiments, the baseline measurement of the migraine associated data is recorded at an interval specified by the individual.

Migraine Associated Data: Environmental Data

In some embodiments, light data comprises a wavelength of light experienced by the individual. In some embodiments, the wavelength of light is on the visible spectrum of light (450 nm-750 nm). In other embodiments, the wavelength of light is not on the visible spectrum of light (e.g. UV light: 100 nm-400 nm). In some embodiments, light data comprises an illuminance of light experienced by the individual.

In some embodiments, sound data comprises a frequency of sound experienced by the individual. In some embodiments, sound data comprises an intensity of sound experienced by the individual.

In some embodiments, temperature data comprises an ambient temperature experienced by the individual. In some embodiments, the ambient temperature ranges from 68° F. to 77° F. (20° C. to 25° C.). In some embodiments, temperature data comprises an outside temperature. In some embodiments, the outside temperature is obtained from an external source, for example from the internet.

In some embodiments, air quality data comprises a level of a contaminant in the air. Examples of air contaminants, by way of non-limiting examples, include ozone, nitrogen dioxide, carbon monoxide, particulate matter ($PM_{10}$ and $PM_{2.5}$), sulphur dioxide, and hydrogen sulphide. In some embodiments, the air quality data is obtained from an external source, for example from the internet.

In some embodiments, humidity data comprises a humidity experienced by the individual.

In some embodiments, barometric pressure data comprises a barometric pressure experienced by the individual. In some embodiments, the barometric pressure data comprises whether the barometric pressure is rising or falling. In some embodiments, the barometric pressure data is obtained from an external source, for example the internet.

In some embodiments, altitude data comprises an altitude of the individual.

In some embodiments, location data comprises a location of the individual. In some embodiments, the location comprises GPS coordinates of the location. In other embodiments, the location comprises a zip code, street, city, or combination thereof. In some embodiments, the location comprises whether the individual is at home, at work, or another location.

Migraine Associated Data: Physiological Data

In some embodiments, heart data comprises a heart rate of the individual. In some embodiments heart data is an electrocardiogram (ECG) of an individual. In some embodiments, heart data comprises whether the individual has an arrhythmia. In some embodiments, heart data comprises heart rate variability.

In some embodiments, activity data comprises a movement. In some embodiments, the movement is the distance an individual has moved during a day. In some embodiments the distance moved is determined for different periods of the time. Examples of periods of time, by way of non-limiting examples, include general (e.g. morning, afternoon, evening, night) and every hour (e.g. 8-9 am, 9-10 am, and so forth). In some embodiments, the movement is a number of steps an individual has taken during the day or during a period of time. In some embodiments, activity data comprises self-reported data regarding an activity in which the individual has participated. In some embodiments, self-reported activity data further comprises the length of time spent participating in the activity. In some embodiments, the activity is chosen by the individual from a list. Example of activities, by way of non-limiting examples, include archery, badminton, baseball, basketball, biking, bowling, canoeing, cricket, cross-country skiing, curling, fencing, football, golf, gymnastics, hiking, hockey, horseback riding, kayaking, martial arts, rollerblading, rowing, running, skating, skiing, snowboarding, snowshoeing, soccer, swimming, tennis, volleyball, weightlifting, and wrestling. In some embodiments, the individual can manually add an activity to the list.

In some embodiments, sleep data comprises an amount of sleep an individual has experienced. In some embodiments, the amount of sleep is automatically recorded or is self-reported. In some embodiments, sleep data comprises a quality of sleep for the individual. In some embodiments, quality of sleep is automatically recorded. In some embodiments, the quality of sleep comprises the amount of movement during sleep. In some embodiments, the quality of sleep comprises the amount of time spent in each stage of sleep. In some embodiments, the quality of sleep comprises the stage of sleep during which an individual awakens. In some embodiments, the quality of sleep is self-reported. In some embodiments, self-reported quality of sleep data comprises a scale of the quality of sleep the individual feels they experienced. A non-limiting example of a scale of quality of sleep is scale of 1 to 5, wherein 1 is a very restful sleep and 5 is a very unrestful sleep. In some embodiments, self-reported quality of sleep data comprises illustrations of facial expressions wherein the facial expressions are representative of the quality of sleep an individual feels they experienced.

In some embodiments, oxygen saturation of the blood comprises an oxygen level of the blood.

In some embodiments, electrodermal activity comprises a measure of galvanic skin response.

Migraine Associated Data: Self-reported Data

In some embodiments, dietary data comprises whether an individual consumed a meal (e.g. breakfast, lunch, dinner) or a snack. In some embodiments, the dietary data comprises a time the meal or snack was consumed. In some embodiments, the dietary data comprises a type of food or beverage consumed. In some embodiments, the dietary data comprises a time a food or beverage was consumed. In some embodiments, the dietary data comprises an amount of the food or beverage consumed. In some embodiments, the type of food or beverage consumed chosen by the individual from a list. Examples of types of food and beverages in the list, by way of non-limiting examples, include chocolate, alcoholic beverages (e.g. red wine, white wine, beer, liquor), caffeine containing beverages (e.g. coffee, soda, tea), avocados, beans (e.g. string, navy, kidney, lima), pickled food (e.g. cucumbers, eggs, beets, olives, peppers), bananas, bread, cheese (e.g. cheddar, blue, Brie, aged cheese), chili pepper, pork, soy-based foods, processed meat (e.g. bacon, hot dogs, deli meats, pepperoni, sausage, jerky), nuts, citrus fruits, dried fruits (e.g. prunes, figs, apricots), vinegar (e.g. red vinegar, balsamic vinegar), apples, pears, plums, apple juice, cider, sour cream, milk, and sweeteners (e.g. aspartame). In some embodiments, the individual can manually add a food or beverage item to the list.

In some embodiments, medication data comprises whether an individual is currently taking a medication. In some embodiments, the medication data comprises a time the medication is taken. In some embodiments, the medication data comprises a quantity of the medication taken. In some embodiments, the medication data is a type of medication taken. In some embodiments, the type of medication taken is chosen by the individual from a list. Examples of medication in the list, by way of non-limiting examples, include pain relievers (e.g. aspirin, ibuprofen, naproxen, acetaminophen), ergots (e.g. dihydroergotamine, ergotamine), triptans (e.g. almotriptan, eletriptan, naratriptan, rizatriptan, sumatriptan, zolmitriptan), opiate-containing medications (e.g. codeine), hormonal contraceptives, and hormone replacement therapy. In some embodiments, the individual can manually add a medication to the list.

In some embodiments, supplement data comprises whether an individual is currently taking a supplement. In some embodiments, the supplement data further comprises a time of day the supplement is taken. In some embodiments, the supplement data further comprises an amount of the supplement taken. In some embodiments, the supplement data is a type of supplement taken. In some embodiments, the type of supplement taken is chosen by the individual from a list. Examples of supplements in the list, by way of non-limiting examples, include vitamin D, vitamin E, vitamin A, vitamin B2, vitamin B3, vitamin B6, vitamin B12, and magnesium, melatonin, butterbur, feverfew, and coenzyme Q10. In some embodiments, the individual can manually add a supplement to the list.

In some embodiments, menstruation status data comprises whether an individual is currently menstruating. In some embodiments, the menstruation status data further comprises the current day of the individual's menstrual cycle, wherein day 1 is the day menstruation began.

In some embodiments, emotional state data comprises the emotional state of an individual. In some embodiments, the emotional state is chosen by the individual from a list. Examples of emotional states in the list, by way of non-limiting examples, include happy, excited, angry, depressed, anxious, confused, and stressed. In some embodiments, the individual can manually add an emotional state to the list. In some embodiments, the emotional state comprises illustrations of facial expressions representing the emotional state.

In some embodiments, pain data comprises the level of pain of a migraine. In some embodiments, the level of pain of a migraine comprises a scale. A non-limiting example of a scale of pain intensity is scale of 1 to 5, wherein 1 is no pain and 5 is severe, debilitating pain. In other embodiments, the level of pain of a migraine data comprises illustrations of facial expressions wherein the facial expressions are representative of the level of pain an individual is feeling.

In some embodiments, location of a migraine data comprises the area of the body where an individual feels migraine pain. In some embodiments, the location of the migraine data comprises an illustration of a body with various regions highlighted where migraine pain can be experienced wherein the individuals selects the illustration best representing where pain is being experienced. In other embodiments, the location of the migraine data comprises an illustration of a body showing a plurality of points where migraine pain can be experienced wherein the individual selects the points where pain is being experienced. In other embodiments, the location of the migraine comprises an illustration of a body showing a plurality of regions where migraine pain can be experienced wherein the individual selects the regions where pain is being experienced.

In some embodiments, biomarker data comprises genetic, proteinic, hormonic, or other biological data. In some embodiments, genetic data comprises the presence of a single nucleotide polymorphism (SNP), insertion, deletion, inversion, microsatellite, or copy number variant. Examples of SNPs associated with migraines include, but are not limited to, rs1835740, rs1043994, rs1042838, rs2651899, rs10166942, and rs11172113. In some embodiments, proteinic data comprises the presence or quantity of a protein biomarker. Non-limiting examples of protein biomarkers include, but are not limited to: C-reactive protein (CRP), calcitonin gene-related protein (cGRP), or adipokines (e.g. adiponectin). In some embodiments, the hormonic data comprises the presence or quantity of a hormone. Examples of hormones include, by way of non-limiting examples, testosterone, progesterone, and estrogen. In some embodiments, the other biological data comprises the level in the individual of a non-protein biomarker. Examples of non-protein biomarkers include, but are not limited to, vitamin D, blood glucose, lipids (e.g. ceramides), insulin, or homocysteine. In some embodiments, the biomarker is determined from a bodily fluid sample from the individual, such as from the blood, saliva, urine, or stool. In some embodiments, the individual reports biomarker data from a family member.

In some embodiments, water intake takes comprises an amount of water consumed by the individual.

Sensor

In some embodiments, the sensor comprises a detector used to collect migraine associated data and a communications element used to transmit migraine associated data collected by the detector to non-transitory computer readable storage media.

In some embodiments, the sensor is located in a computing device. In some embodiments, the computing device is a mobile device, smart phone, smart watch, wearable device, or a combination thereof. Examples of wearable devices, by way of non-limiting examples, include devices manufactured by Fitbit®, Jawbone®, Timex®, Garmin®, Omron®, ReliOn®, and Panasonic®. In some embodiments, the sensor is a free-standing sensor. Examples of a freestanding sensor, by way of non-limiting examples, include: air pollution sensors and weather sensors.

In some embodiments, the detector comprises a photodetector, a lux meter, a sound level meter, a thermometer, an air pollution sensor, a hygrometer, a barometer, an altimeter, an accelerometer, a gyroscope, a heart rate sensor, a clock or some other time monitoring device, a GPS, or any combination thereof.

In some embodiments, the sensor comprises a communications element. In some embodiments, the communications element is used to transmit the migraine associated data to non-transitory computer readable storage media. In some embodiments, the sensor transmits the migraine associated data to the non-transitory computer readable storage media through a wired connection. In some embodiments, the sensor transmits the migraine associated data to the non-transitory computer readable storage media through a wireless connection.

Non-transitory Computer Readable Storage Media

In some embodiments, the platforms and methods disclosed herein include a non-transitory computer readable storage media encoded with a program including instructions executable by the operating system of an optionally networked computing device. In further embodiments, the non-transitory computer readable storage media is a tangible component of a computing device. In still further embodiments, the non-transitory computer readable storage media is optionally removable from a computing device. In some embodiments, the non-transitory computer readable storage media includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the non-transitory computer readable storage media is encoded with a computer program including instructions executable by a processor to create an application comprising: a software module used to receive the migraine associated data from the sensor; and a software module used to present an interface allowing the user to interact with the migraine associated data. In some embodiments, the non-transitory computer readable storage media further comprises a software module to present an interface allowing the individual to manually input self-reported migraine associated data. In some embodiments, the non-transitory computer readable storage media further comprises a software module to collect a migraine associated data from an external source, such as the internet. In some embodiments, the non-transitory computer readable storage media further comprises a software module used to present an interface allowing the individual to provide manual instructions regarding collection of migraine associated data. In some embodiments, providing manual instructions regarding migraine associated data collection comprises the individual determining when baseline measurements of migraine associated data are recorded. In some embodiments, baseline measurements of migraine associated data are take one, two, three, four, five, six, seven, eight, nine, ten, twelve, twenty four, or forty eight times per day. In some embodiments, the baseline measurement of the migraine associated data is recorded at an interval specified by the individual.

In some embodiments, interacting with the migraine associated data comprises the individual sorting the data, for example by type of migraine associated data, date collected, proximity in occurrence to a migraine. In some embodiments, interacting with the migraine associated comprises the individual downloading the data. In some embodiments, the data comprises the raw data. In some embodiments, the non-transitory computer readable storage media further comprises a software module used to apply an algorithm to the raw migraine associated data to generate analytic data comprising trends of one or more migraine associated data or correlations of one or more migraine associated data with occurrence of migraines wherein such trends or correlations are presented in a report. In other embodiments, the non-transitory computer readable storage media further comprises a software module used to parse and clean the migraine associated data, the cleaning comprising removing erroneous data, removing outlier data, flagging erroneous data, interpolating missing data, and flagging outlier data. In further embodiments, the non-transitory computer readable storage media further comprises a software module used to apply an algorithm to the cleaned migraine associated data to generate analytic data comprising trends of one or more migraine associated data or correlations of one or more migraine associated data with occurrence of migraines wherein such trends or correlations are presented in a report. In some embodiments, the non-transitory computer readable storage media further comprises a software module used to send a notification to a computing device when the sensor senses a migraine associated data above a specific threshold or within a specific range.

In some embodiments, the non-transitory computer readable storage media transmits the migraine associated data from the memory of the media to a server. In some embodiments, the migraine associated data from a plurality of individuals is aggregated on the server.

Ocular Device

In some embodiments, the platform further comprises an ocular device for reducing the occurrence, duration, or severity of migraine headaches in the individual in need thereof, operatively connected to the non-transitory computer readable storage media and the sensor, comprising: (a) a first mode that allows a target light wavelength or a target light intensity to pass through the first lens; (b) a second mode that reduces or substantially blocks the target light wavelength or the target light intensity from passing through the first lens; (c) a voltage source operatively coupled to the first lens and configured to generate a voltage, wherein application of the voltage to the first lens switches the first lens form the first mode to the second mode; and (d) an activator operatively coupled to the voltage source, and configured to activate the voltage source upon receipt of a signal from a signal receiver; wherein the target light wavelength or the target light intensity is associated with an occurrence of migraine headaches in the individual.

Lens

In some embodiments, the first lens further comprises an electrochromic compound. As used herein, an electrochromic compound means a compound that changes color after activation. Activation of an electrochromic compound results in a change of electronic state. The change of electronic state is achieved through reduction (absorbing electrons) or oxidation (loosing electrons). Examples of electrochromic compounds include, by way of non-limiting examples, inorganic materials, such as tungsten oxide, nickel oxide, titanium oxide, niobium oxide, zinc oxide, tantalum oxide, iron oxide, chromium oxide, manganese oxide, iridium oxide, vanadium oxide, rhodium oxide, molybdenum oxide, cobalt oxide, cerium oxide, silver oxide, or ruthenium oxide and organic materials, such as poly(3, 4-ethylenedioxythiophene) (PEDOT), poly(ethylenedioxy-thiophene-didodecyloxybenzene) (PEB),poly(ethylene oxide)(PEO), poly(methyl metacrylate)(PMMA), polyvinylidene difluoride (PVDF) polyaniline, viologen, KFe[Fe(CN)$_6$], Fe$_4$[Fe(CN)$_6$]$_3$, Fe$_4$[Ru(CN)$_6$]$_3$, CoFe$_4$(CN)$_6$, InFe$_4$(CN)$_6$, pyrazoline, and tetrathiafulvalene.

In some embodiments, the first lens further comprises an electrochromic compound. In some embodiments, the first lens comprises an electrochromic compound selected from the group consisting of tungsten oxide, nickel oxide, titanium oxide, niobium oxide, zinc oxide, tantalum oxide, iron oxide, chromium oxide, manganese oxide, iridium oxide, vanadium oxide, rhodium oxide, molybdenum oxide, cobalt oxide, cerium oxide, silver oxide, ruthenium oxide, poly(3,4-ethylenedioxythiophene) (PEDOT), poly(ethylene oxide) (PEO), poly(ethylenedioxythiophene-didodecyloxybenzene) (PEB),poly(methyl metacrylate)(PMMA), polyvinylidene difluoride (PVDF) polyaniline, viologen, KFe[Fe(CN)$_6$], Fe$_4$[Fe(CN)$_6$]$_3$, Fe$_4$[Ru(CN)$_6$]$_3$, CoFe$_4$(CN)$_6$, InFe$_4$(CN)$_6$, pyrazoline, and tetrathiafulvalene. In some embodiments, a first mode allows a target light wavelength or a target light intensity to pass through the first lens. In some embodiments, a second mode reduces or substantially blocks a target light wavelength or a target light intensity from passing through the first lens.

In some embodiments, the ocular device further comprises a second lens. In some embodiments, the second lens operates is operatively coupled to the voltage source. In some embodiments the second lens is operatively connected to the first lens. In some embodiments, the second lens further comprises an electrochromic compound as described herein. In some embodiments, the second lens further comprises an electrochromic compound identical to the electrochromic compound of the first lens. In some embodiments, the first lens and/or the second lens is a corrective lens. In some embodiments, the first lens and/or the second lens is a bifocal lens.

In some embodiments, the light that triggers or amplifies the pain caused by a migraine is a target wavelength. In some embodiments, the target wavelength is the visible spectrum of light. In some embodiments, the target wavelength is blue light (450 nm-495 nm). In some embodiments, the target wavelength is red light (620 nm-750 nm). In some embodiments the target wavelength is blue and red light. In some embodiments, the target wavelength is UV light (100 nm-400 nm). In some embodiments, the target wavelength is a wavelength determined by the subject.

In some embodiments, the light that triggers or amplifies the pain caused by a migraine is a target light intensity. In some embodiments, the target light intensity is direct sunlight (32,000 lux-100,000 lux). In some embodiments, the target light intensity is a light intensity determined by the subject.

Voltage Source

In some embodiments, the voltage source is operatively coupled to the voltage regulator and is configured to generate a voltage. In some embodiments, the voltage source is a battery. In some embodiments, the voltage source is rechargeable. In some embodiments, the voltage source is removable.

Activator

In some embodiments, the activator comprises a signal receiver. In some embodiments, the activator is operatively coupled to the first lens and the voltage source. In some embodiments, the activator is configured to activate the voltage source upon receipt of a signal from the signal receiver. In some embodiments, the activator is wirelessly coupled to the voltage source and emits a wireless signal received by the voltage source. In some embodiments, the activator further comprises a signal receiver.

Voltage Regulator

In some embodiments, a voltage regulator is operatively coupled to the first lens. In some embodiments, the voltage regulator is configured to modulate a voltage to a target voltage. In some embodiments, application of the target voltage to the first lens switches the first lens from the first mode to the second mode. In some embodiments, the voltage regulator generates voltage at a fixed voltage. In some embodiments, the voltage regulator generates pulses of fixed voltages.

Current Regulator

In some embodiments, a current regulator is operatively coupled to the voltage source. In some embodiments, the current regulator is configured to regulate the current applied to the first lens.

Charging Circuit

In some embodiments, a charging circuit is operatively coupled to the voltage source. In some embodiments, the charging circuit is configured to provide power to the voltage source when power is received from a power source. In some embodiments, the power source is electricity obtained from an electrical outlet. In some embodiments, the power source is electricity obtained from a battery. In some embodiments, the power is transmitted to the charging circuit by any suitable means. In some embodiments, the power is transmitted to the charging circuit by a wireless charging technology. In some embodiments, the wireless charging technology is inductive charging or conductive charging.

Signal Receiver

In some embodiments, the signal receiver is a sensor pad, wireless element, photosensor or a physiological sensor. In some embodiments, the physiological sensor is a pulse sensor, a blood pressure sensor, a body temperature sensor, a perspiration sensor, a pulse oximeter, a GSR amplifier, a finger electrode, or any combinations thereof.

In some embodiments, the signal receiver is a wireless element. In some embodiments, the wireless element is configured to receive a signal from a computing device for example a mobile device. In some embodiments, the signal receiver is a wireless element which is configured to receive a signal from a physiological sensor attached to skin of the subject. In some embodiments, detecting the target light wavelength or target light intensity comprises the subject detecting the target light wavelength or target light intensity and activating the computer program such that the wireless element emits a signal which is received by the activator.

In some embodiments, the wireless element is a wireless network technology. In some embodiments, the wireless network technology is ANT, ANT+, INSTEON, IrDA, Wireless USB, Bluetooth, Z-Wave, or ZigBee, IEEE 802.15.4, 6LoWPAN, or Wi-Fi.

Sensor Pad

In some embodiments, the signal receiver is a sensor pad. In some embodiments the subject detects the target wavelength and activates the sensor pad such that the sensor pad emits a signal which is received by the activator. In some embodiments, the sensor pad is a button, dial, switch, touch screen, or microphone. In some embodiments, a button is engaged by pressing on the button. In some embodiments, a dial is engaged by turning the dial. In some embodiments, the switch is engaged by pressing or toggling the switch. In some embodiments, a touch screen is engaged by touching a surface utilizing a touch detection technology. In some embodiments, the touch detection technology includes resistive, capacitive, infrared, surface acoustic wave, and near field imaging technologies.

Photosensor

In some embodiments, the signal receiver is a photosensor. In some embodiments, the photosensor is configured to signal the activator upon detecting the target light wavelength or the target light intensity. In some embodiments, detecting the target light wavelength or the target light intensity comprises the photosensor detecting the target light wavelength or target light intensity and emitting a signal which is received by the activator. In some embodiments, the photosensor is a semiconductor device that converts light into current. In some embodiments, the photosensor is a photodiode, a bipolar phototransistor, or a photosensitive field-effect transistor.

Physiological Sensor

In some embodiments, the signal receiver is a physiological sensor. In some embodiments, the physiological sensor is a pulse sensor. Examples of pulse sensors include, by way of non-limiting examples, devices manufactured by Fitbit®, Jawbone®, Polar®, Timex®, and Garmin®, as well as pulse sensors programed and operated via an Arduino chip. In some embodiments, the physiological sensor is configured to signal the activator upon detecting a target physiological property of the subject. In some embodiments, the physiological property is a change in pulse, an elevated pulse, an erratic pulse, or a lowered pulse. In some embodiments the physiological sensor is a pulse sensor configured to signal the activator upon detecting a target pulse of the subject. In some embodiments, detecting the target light wavelength or the target light intensity comprises the pulse sensor detecting a pulse of the subject and emitting a signal which is received by the activator.

In some embodiments, the physiological sensor is a blood pressure sensor. Examples of blood pressure sensors include, by way of non-limiting examples, devices manufactured by Omron®, ReliOn®, Panasonic®, and Veridian®. In some embodiments, the physiological sensor is configured to signal the activator upon detecting a target physiological property of the subject. In some embodiments, the physiological property is a change in blood pressure, an elevated blood pressure, or a lowered blood pressure. In some embodiments the physiological sensor is a blood pressure sensor configured to signal the activator upon detecting a target blood pressure of the subject. In some embodiments, detecting the target wavelength comprises the blood pressure sensor detecting a blood pressure of the subject and emitting a signal which is received by the activator.

In some embodiments the physiological sensor is a perspiration sensor. In some embodiments, the physiological sensor is configured to signal the activator upon detecting a target physiological property of the subject. In some embodiments, the physiological property is a change in perspiration level or an elevated perspiration level. In some embodiments the physiological sensor is a perspiration sensor configured to signal the activator upon detecting the perspiration level of the subject. In some embodiments, detecting the perspiration level comprises the perspiration sensor detecting the perspiration level of the subject and emitting a signal which is received by the activator.

In some embodiments the physiological sensor is a body temperature sensor. In some embodiments, the physiological sensor is configured to signal the activator upon detecting a target physiological property of the subject. In some embodiments, the physiological property is a change in body temperature, an elevated body temperature, or a lowered body temperature. In some embodiments the physiological sensor is a body temperature sensor configured to signal the activator upon detecting the body temperature of the subject. In some embodiments, detecting the body temperature level comprises the body temperature sensor detecting the body temperature of the subject and emitting a signal which is received by the activator.

In some embodiments, the physiological sensor detects multiple physiological characteristics.

Computing Device

In some embodiments, the computing device is a mobile device. In some embodiments, the mobile device is a smart phone or a smart watch. In some embodiments, the computer program is a mobile application. In some embodiments, the mobile application is provided to a mobile device at the time it is manufactured. In other embodiments, the mobile application is provided to a mobile device via a computer network.

In some embodiments, the computing device further comprises an operating system configured to perform executable instructions. The operating system is, for example, software, including programs and data, which manages the device's hardware and provides services for execution of applications. Suitable personal computer operating systems include, by way of non-limiting examples, Microsoft® Windows®, Apple OS X®, UNIX®, and UNIX-like operating systems such as GNU/Linux®. In some embodiments, the operating system is provided by cloud computing. Suitable mobile smart phone operating systems include, by way of non-limiting examples, Nokia® Symbian® OS, Apple® iOS®, Research In Motion® BlackBerry OS®, Google® Android Microsoft® Windows Phone OS, Microsoft® Windows Mobile® OS, Linux®, and Palm® WebOS®.

In some embodiments, the computing device further comprises a memory device. In some embodiments, the processing device includes a memory device. A memory device is one or more physical apparatus used to store data or programs on a temporary basis, a permanent basis, or combinations thereof. In some embodiments, a memory device is volatile and requires power to maintain stored information. In some embodiments, a memory device is non-volatile and retains stored information and does not require power to maintain stored information.

In some embodiments, the computing device further comprises a display to provide visual information to a user. In some embodiments, a display is a cathode ray tube (CRT). In some embodiments, a display is a liquid crystal display (LCD). In further embodiments, a display is a thin film transistor liquid crystal display (TFT-LCD). In some embodiments, a display is an organic light emitting diode (OLED) display. In various further embodiments, on OLED display is a passive-matrix OLED (PMOLED) or active-matrix OLED (AMOLED) display. In some embodiments, a display is a plasma display. In other embodiments, a display is a video projector. In still further embodiments, a display is a combination of devices such as those disclosed herein.

In some embodiments, the computing device further comprises an input device to receive information from a user. In some embodiments, an input device is a keyboard or keypad. In some embodiments, an input device is a pointing device including, by way of non-limiting examples, a mouse, trackball, track pad, joystick, game controller, or stylus. In some embodiments, an input device is a touch screen or a multi-touch screen. In other embodiments, an input device is a microphone to capture voice or other sound input. In other embodiments, an input device is a video camera to capture motion or visual input. In still further embodiments, an input device is a combination of devices such as those disclosed herein.

In accordance with the description herein, suitable computing devices include, by way of non-limiting examples, desktop computers, laptop computers, notebook computers, tablet computers, netbook computers, smart book computers, subnotebook computers, ultra-mobile PCs, handheld computers, personal digital assistants, Internet appliances, smart phones, music players, and portable video game systems. Many mobile smart phones are suitable for use in the systems described herein. Suitable tablet computers include those with booklet, slate, and convertible configurations. Suitable portable video game systems include, by way of non-limiting examples, Nintendo DS™ and Sony® PSP™.

In some embodiments, the software module is created by techniques known to those of skill in the art using machines, software, and languages known to the art. The software modules disclosed herein are implemented in a multitude of ways. In various embodiments, the one or more software modules comprise, by way of non-limiting examples, a web application, a mobile application, and a standalone application. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Further disclosed herein, in certain embodiments, are methods for reducing or substantially blocking an unwanted light from being perceived by a subject in need thereof comprising: receiving an ocular device comprising: a first lens; a first mode that allows a target light wavelength or a target light intensity to pass through the first lens; a second mode that reduces or substantially blocks the target light wavelength or the target light intensity from passing through the first lens; a voltage source operatively coupled to the first lens and configured to generate a voltage, wherein application of the voltage to the first lens switches the first lens from the first mode to the second mode; and an activator operatively coupled to the voltage source, and configured to activate the voltage source upon receipt of a signal from a signal receiver; wearing the ocular device in conditions typically associated with unwanted light, detecting, manually or automatically, the unwanted light, changing, manually or automatically, from the first mode to the second mode when the unwanted light is detected.

Method

Described herein, in certain embodiments, are methods of recording migraine associated data for an individual who experiences migraines comprising the steps of: receiving a sensor operatively connected to a non-transitory computer-readable storage media; and instructing of the non-transitory computer readable storage media to signal the sensor to record the migraine associated data, wherein recording the migraine associated data comprises: recording of the migraine associated data by the sensor; transmitting the migraine associated data from the sensor to the non-transitory computer readable storage media; and storing the migraine associated data on a memory of the non-transitory computer readable storage media.

Migraine Associated Data

In some embodiments, the migraine associated data comprises environmental data. In some embodiments, the environmental data is selected from the group consisting of: light, sound, temperature, air quality, humidity, barometric pressure, altitude, location data, or any combination thereof. In some embodiments, the migraine associated data comprises physiological data. In some embodiments the physiological data is selected from the group consisting of: heart, activity, sleep data, oxygen saturation of the blood, and electrodermal activity or any combination thereof. In some embodiments, the migraine associated data comprises self-reported data. In some embodiments the self-reported data is selected from the group consisting of diet, medication, vitamins, supplements, menstruation status, emotional state, pain intensity, migraine location, sleep, activity, biomarker, water intake, or any combination thereof. In some embodiments, the migraine associated data is recorded when the sensor is triggered automatically. In some embodiments, the measurement of migraine associated data is taken when the sensor is triggered manually. In some embodiments, the migraine associated data is taken as a baseline measurement. In some embodiments, the migraine associated data is taken instantaneously when the sensor is triggered. In some embodiments, the measure of migraine associated data is taken over a period of time after the sensor is triggered. In some embodiments, the baseline measure of migraine associated data is recorded one, two, three, four, five, six, seven, eight, nine, ten, twelve, twenty four, or forty eight times per day. In some embodiments, the baseline measurement of the migraine associated data is recorded at an interval specified by the individual.

Sensor

In some embodiments, the sensor comprises a detector used to collect migraine associated data and a communications element used to transmit migraine associated data collected by the detector to non-transitory computer readable storage media.

In some embodiments, the sensor is located in a computing device. In some embodiments, the computing device is a mobile device, smart phone, smart watch, wearable device, or a combination thereof. Examples of wearable devices, by way of non-limiting examples, include devices manufactured by Fitbit®, Jawbone®, Timex®, Garmin®, Omron®, ReliOn®, and Panasonic®. In some embodiments, the sensor is a free-standing sensor. Examples of a freestanding sensor, by way of non-limiting examples, include: air pollution sensors and weather sensors.

In some embodiments, the detector comprises a photodetector, a lux meter, a sound level meter, a thermometer, an air pollution sensor, a hygrometer, a barometer, an altimeter, an accelerometer, a gyroscope, a heart rate sensor, a clock or some other time monitoring device, a GPS, or any combination thereof.

In some embodiments, the sensor comprises a communications element. In some embodiments, the communications element is used to transmit the migraine associated data to non-transitory computer readable storage media. In some embodiments, the sensor transmits the migraine associated data to the non-transitory computer readable storage media through a wired connection. In some embodiments, the sensor transmits the migraine associated data to the non-transitory computer readable storage media through a wireless connection.

Non-transitory Computer Readable Storage Media

In some embodiments, the platforms and methods disclosed herein include a non-transitory computer readable storage media encoded with a program including instructions executable by the operating system of an optionally networked computing device. In further embodiments, the non-transitory computer readable storage media is a tangible component of a computing device. In still further embodiments, the non-transitory computer readable storage media is optionally removable from a computing device. In some embodiments, the non-transitory computer readable storage media includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the non-transitory computer readable storage media is encoded with a computer program including instructions executable by a processor to create an application comprising: a software module used to receive the migraine associated data from the sensor; and a software module used to present an interface allowing the user to interact with the migraine associated data. In some embodiments, the non-transitory computer readable storage media further comprises a software module to present an interface allowing the individual to manually input self-reported migraine associated data. In some embodiments, the non-transitory computer readable storage media further comprises a software module to collect a migraine associated data from an external source, such as the internet. In some embodiments, the non-transitory computer readable storage media further comprises a software module used to present an interface allowing the individual to provide manual instructions regarding collection of migraine associated data. In some embodiments, providing manual instructions regarding migraine associated data collection comprises the individual determining when baseline measurements of migraine associated data are recorded. In some embodiments, baseline measurements of migraine associated data are take one, two, three, four, five, six, seven, eight, nine, ten, twelve, twenty four, or forty eight times per day. In some embodiments, the baseline measurement of the migraine associated data is recorded at an interval specified by the individual.

In some embodiments, interacting with the migraine associated data comprises the individual sorting the data, for example by type of migraine associated data, date collected, proximity in occurrence to a migraine. In some embodiments, interacting with the migraine associated comprises the individual downloading the data. In some embodiments, the data comprises the raw data. In some embodiments, the non-transitory computer readable storage media further comprises a software module used to apply an algorithm to the raw migraine associated data to generate analytic data comprising trends of one or more migraine associated data or correlations of one or more migraine associated data with occurrence of migraines wherein such trends or correlations are presented in a report. In other embodiments, the non-transitory computer readable storage media further comprises a software module used to parse and clean the migraine associated data, the cleaning comprising removing erroneous data, removing outlier data, flagging erroneous data, interpolating missing data, and flagging outlier data. In further embodiments, the non-transitory computer readable storage media further comprises a software module used to apply an algorithm to the cleaned migraine associated data to generate analytic data comprising trends of one or more migraine associated data or correlations of one or more migraine associated data with occurrence of migraines wherein such trends or correlations are presented in a report. In some embodiments, the non-transitory computer readable storage media further comprises a software module used to send a notification to a computing device when the sensor senses a migraine associated data above a specific threshold or within a specific range.

In some embodiments, the non-transitory computer readable storage media transmits the migraine associated data from the memory of the media to a server. In some embodiments, the migraine associated data from a plurality of individuals is aggregated on the server.

Ocular Device

In some embodiments, the platform further comprises an ocular device for reducing the occurrence, duration, or severity of migraine headaches in the individual in need thereof, operatively connected to the non-transitory computer readable storage media and the sensor, comprising: (a) a first mode that allows a target light wavelength or a target light intensity to pass through the first lens; (b) a second mode that reduces or substantially blocks the target light wavelength or the target light intensity from passing through the first lens; (c) a voltage source operatively coupled to the first lens and configured to generate a voltage, wherein application of the voltage to the first lens switches the first lens form the first mode to the second mode; and (d) an activator operatively coupled to the voltage source, and configured to activate the voltage source upon receipt of a signal from a signal receiver; wherein the target light wavelength or the target light intensity is associated with an occurrence of migraine headaches in the individual.

Lens

In some embodiments, the first lens further comprises an electrochromic compound. As used herein, an electrochromic compound means a compound that changes color after activation. Activation of an electrochromic compound results in a change of electronic state. The change of electronic state is achieved through reduction (absorbing electrons) or oxidation (loosing electrons). Examples of electrochromic compounds include, by way of non-limiting examples, inorganic materials, such as tungsten oxide, nickel oxide, titanium oxide, niobium oxide, zinc oxide, tantalum oxide, iron oxide, chromium oxide, manganese oxide, iridium oxide, vanadium oxide, rhodium oxide, molybdenum oxide, cobalt oxide, cerium oxide, silver oxide, or ruthenium oxide and organic materials, such as poly(3,4-ethylenedioxythiophene) (PEDOT), poly(ethylenedioxy-thiophene-didodecyloxybenzene) (PEB),poly(ethylene oxide)(PEO), poly(methyl metacrylate)(PMMA), polyvinylidene difluroide (PVDF) polyaniline, viologen, $KFe[Fe(CN)_6]$, $Fe_4[Fe(CN)_6]_3$, $Fe_4[Ru(CN)_6]_3$, $CoFe_4(CN)_6$, $InFe_4(CN)_6$, pyrazoline, and tetrathiafulvalene.

In some embodiments, the first lens further comprises an electrochromic compound. In some embodiments, the first lens comprises an electrochromic compound selected from the group consisting of tungsten oxide, nickel oxide, titanium oxide, niobium oxide, zinc oxide, tantalum oxide, iron oxide, chromium oxide, manganese oxide, iridium oxide, vanadium oxide, rhodium oxide, molybdenum oxide, cobalt oxide, cerium oxide, silver oxide, ruthenium oxide, poly(3, 4-ethylenedioxythiophene) (PEDOT), poly(ethylene oxide) (PEO), poly(ethylenedioxythiophene-didodecyloxybenzene) (PEB),poly(methyl metacrylate)(PMMA), polyvinylidene difluroide (PVDF) polyaniline, viologen, $KFe[Fe(CN)_6]$, $Fe_4[Fe(CN)_6]_3$, $Fe_4[Ru(CN)_6]_3$, $CoFe_4(CN)_6$, $InFe_4(CN)_6$, pyrazoline, and tetrathiafulvalene. In some embodiments, a first mode allows a target light wavelength or a target light intensity to pass through the first lens. In some embodiments, a second mode reduces or substantially blocks a target light wavelength or a target light intensity from passing through the first lens.

In some embodiments, the ocular device further comprises a second lens. In some embodiments, the second lens operates is operatively coupled to the voltage source. In some embodiments the second lens is operatively connected to the first lens. In some embodiments, the second lens further comprises an electrochromic compound as described herein. In some embodiments, the second lens further comprises an electrochromic compound identical to the electrochromic compound of the first lens. In some embodiments, the first lens and/or the second lens is a corrective lens. In some embodiments, the first lens and/or the second lens is a bifocal lens.

In some embodiments, the light that triggers or amplifies the pain caused by a migraine is a target wavelength. In some embodiments, the target wavelength is the visible spectrum of light. In some embodiments, the target wavelength is blue light (450 nm-495 nm). In some embodiments, the target wavelength is red light (620 nm-750 nm). In some embodiments the target wavelength is blue and red light. In some embodiments, the target wavelength is UV light (100 nm-400 nm). In some embodiments, the target wavelength is a wavelength determined by the subject.

In some embodiments, the light that triggers or amplifies the pain caused by a migraine is a target light intensity. In some embodiments, the target light intensity is direct sunlight (32,000 lux-100,000 lux). In some embodiments, the target light intensity is a light intensity determined by the subject.

Voltage Source

In some embodiments, the voltage source is operatively coupled to the voltage regulator and is configured to generate a voltage. In some embodiments, the voltage source is a battery. In some embodiments, the voltage source is rechargeable. In some embodiments, the voltage source is removable.

Activator

In some embodiments, the activator comprises a signal receiver. In some embodiments, the activator is operatively coupled to the first lens and the voltage source. In some embodiments, the activator is configured to activate the voltage source upon receipt of a signal from the signal receiver. In some embodiments, the activator is wirelessly coupled to the voltage source and emits a wireless signal received by the voltage source. In some embodiments, the activator further comprises a signal receiver.

Voltage Regulator

In some embodiments, a voltage regulator is operatively coupled to the first lens. In some embodiments, the voltage regulator is configured to modulate a voltage to a target voltage. In some embodiments, application of the target voltage to the first lens switches the first lens from the first mode to the second mode. In some embodiments, the voltage regulator generates voltage at a fixed voltage. In some embodiments, the voltage regulator generates pulses of fixed voltages.

Current Regulator

In some embodiments, a current regulator is operatively coupled to the voltage source. In some embodiments, the current regulator is configured to regulate the current applied to the first lens.

Charging Circuit

In some embodiments, a charging circuit is operatively coupled to the voltage source. In some embodiments, the charging circuit is configured to provide power to the voltage source when power is received from a power source. In some embodiments, the power source is electricity obtained from an electrical outlet. In some embodiments, the power source is electricity obtained from a battery. In some embodiments, the power is transmitted to the charging circuit by any suitable means. In some embodiments, the power is transmitted to the charging circuit by a wireless charging technology. In some embodiments, the wireless charging technology is inductive charging or conductive charging.

Signal Receiver

In some embodiments, the signal receiver is a sensor pad, wireless element, photosensor or a physiological sensor. In some embodiments, the physiological sensor is a pulse sensor, a blood pressure sensor, a body temperature sensor, a perspiration sensor, a pulse oximeter, a GSR amplifier, a finger electrode, or any combinations thereof.

In some embodiments, the signal receiver is a wireless element. In some embodiments, the wireless element is configured to receive a signal from a computing device for example a mobile device. In some embodiments, the signal receiver is a wireless element which is configured to receive a signal from a physiological sensor attached to skin of the subject. In some embodiments, detecting the target light wavelength or target light intensity comprises the subject detecting the target light wavelength or target light intensity and activating the computer program such that the wireless element emits a signal which is received by the activator.

In some embodiments, the wireless element is a wireless network technology. In some embodiments, the wireless network technology is ANT, ANT+, INSTEON, IrDA, Wireless USB, Bluetooth, Z-Wave, or ZigBee, IEEE 802.15.4, 6LoWPAN, or Wi-Fi.

Sensor Pad

In some embodiments, the signal receiver is a sensor pad. In some embodiments the subject detects the target wavelength and activates the sensor pad such that the sensor pad emits a signal which is received by the activator. In some embodiments, the sensor pad is a button, dial, switch, touch screen, or microphone. In some embodiments, a button is engaged by pressing on the button. In some embodiments, a dial is engaged by turning the dial. In some embodiments, the switch is engaged by pressing or toggling the switch. In some embodiments, a touch screen is engaged by touching a surface utilizing a touch detection technology. In some embodiments, the touch detection technology includes resistive, capacitive, infrared, surface acoustic wave, and near field imaging technologies.

Photosensor

In some embodiments, the signal receiver is a photosensor. In some embodiments, the photosensor is configured to signal the activator upon detecting the target light wavelength or the target light intensity. In some embodiments, detecting the target light wavelength or the target light intensity comprises the photosensor detecting the target light wavelength or target light intensity and emitting a signal which is received by the activator. In some embodiments, the photosensor is a semiconductor device that converts light into current. In some embodiments, the photosensor is a photodiode, a bipolar phototransistor, or a photosensitive field-effect transistor.

Physiological Sensor

In some embodiments, the signal receiver is a physiological sensor. In some embodiments, the physiological sensor is a pulse sensor. Examples of pulse sensors include, by way of non-limiting examples, devices manufactured by Fitbit®, Jawbone®, Polar®, Timex®, and Garmin®, as well as pulse sensors programed and operated via an Arduino chip. In some embodiments, the physiological sensor is configured to signal the activator upon detecting a target physiological property of the subject. In some embodiments, the physiological property is a change in pulse, an elevated pulse, an erratic pulse, or a lowered pulse. In some embodiments the physiological sensor is a pulse sensor configured to signal the activator upon detecting a target pulse of the subject. In some embodiments, detecting the target light wavelength or the target light intensity comprises the pulse sensor detecting a pulse of the subject and emitting a signal which is received by the activator.

In some embodiments, the physiological sensor is a blood pressure sensor. Examples of blood pressure sensors include, by way of non-limiting examples, devices manufactured by Omron®, ReliOn®, Panasonic®, and Veridian®. In some embodiments, the physiological sensor is configured to signal the activator upon detecting a target physiological property of the subject. In some embodiments, the physiological property is a change in blood pressure, an elevated blood pressure, or a lowered blood pressure. In some embodiments the physiological sensor is a blood pressure sensor configured to signal the activator upon detecting a target blood pressure of the subject. In some embodiments, detecting the target wavelength comprises the blood pressure sensor detecting a blood pressure of the subject and emitting a signal which is received by the activator.

In some embodiments the physiological sensor is a perspiration sensor. In some embodiments, the physiological sensor is configured to signal the activator upon detecting a target physiological property of the subject. In some embodiments, the physiological property is a change in perspiration level or an elevated perspiration level. In some embodiments the physiological sensor is a perspiration sensor configured to signal the activator upon detecting the perspiration level of the subject. In some embodiments, detecting the perspiration level comprises the perspiration sensor detecting the perspiration level of the subject and emitting a signal which is received by the activator.

In some embodiments the physiological sensor is a body temperature sensor. In some embodiments, the physiological sensor is configured to signal the activator upon detecting a target physiological property of the subject. In some embodiments, the physiological property is a change in body temperature, an elevated body temperature, or a lowered body temperature. In some embodiments the physiological sensor is a body temperature sensor configured to signal the activator upon detecting the body temperature of the subject. In some embodiments, detecting the body temperature level comprises the body temperature sensor detecting the body temperature of the subject and emitting a signal which is received by the activator.

In some embodiments, the physiological sensor detects multiple physiological characteristics.

Computing Device

In some embodiments, the computing device is a mobile device. In some embodiments, the mobile device is a smart phone or a smart watch. In some embodiments, the computer program is a mobile application. In some embodiments, the mobile application is provided to a mobile device at the time it is manufactured. In other embodiments, the mobile application is provided to a mobile device via a computer network.

Turning now to FIG. 1, this figure presents a process flow diagram for mobile device processes for capturing, recording and transmitting sensor and event record data. In an embodiment, a mobile device 100 such as a smart phone, tablet, iPad, smart watch, or other mobile device capable of networked data communication, may initiate a process 1 to capture sensor data. In a non-limiting example, process 1 may receive data signals from a sensor, as previously described, and record the sensor data signals 104 in the electronic memory of the mobile device 100. Process 1 may then transmit the recorded sensor data signals 106 through a data communications device 108 embedded within the mobile device 100 to a system server 110. The system server 100 may then store the received sensor data signals in an electronic storage device associated with the system server 100.

The mobile device may also initiate a Process 2 to capture event records entered by a user, provider, medical professional, or caretaker. In a non-limiting example, process 2 may receive and accept migraine event record data 112 as entered into the mobile device. The migraine event record data may be recorded and stored 114 in the electronic memory of the mobile device 100. Process 2 may then transmit the recorded and stored event record data 116 through a data communications device 108 embedded within the mobile device 100 to a system server 110. The system server 100 may then store the received event record data in an electronic storage device associated with the system server 110.

Figure 2:
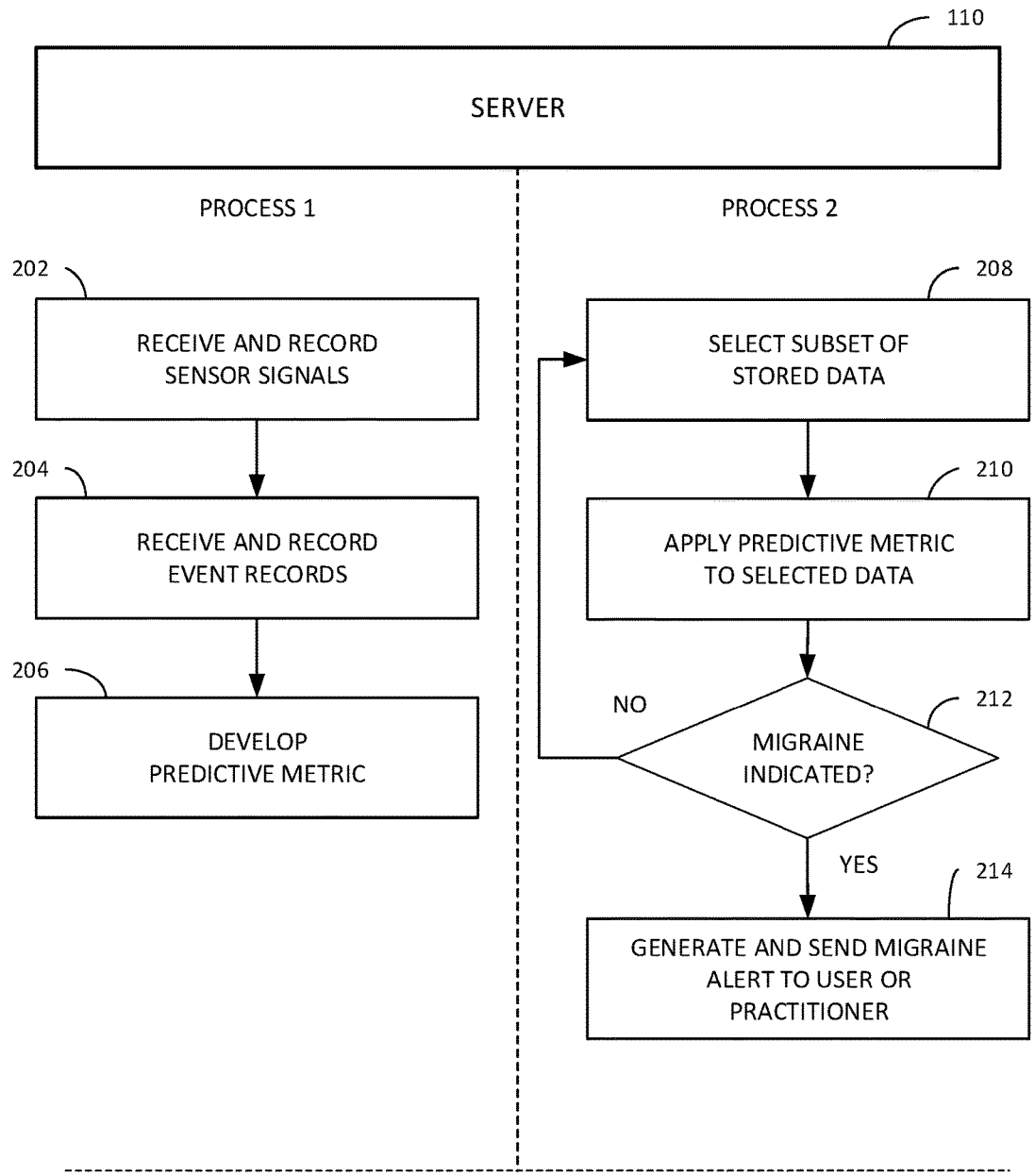
FIG. 2 is a process flow diagram for processes active on a system server for capturing sensor and event data and generating a migraine alert consistent with certain embodiments of the present invention.

Turning now to FIG. 2, this figure presents a process flow diagram for processes active on a system server for capturing sensor and event data and generating a migraine alert. In an embodiment, the system server 110 may initiate a process 1 to receive and record sensor signals 202 and receive and record event records 204. The system server 110 may then utilize the received sensor signals and event records to analyze the received information and develop a predictive metric 206 that is indicative of a migraine occurrence.

The system server 110 may initiate a process 2 to utilize the developed predictive metric to provide user alerts. The system server 110 may select a subset of the data stored within the electronic storage device associated with the system server for analysis 208. The system server 110 may apply the predictive metric previously developed 210 to the selected subset of data. The system server 110 determine that a migraine episode has not occurred if the predictive metric threshold for a migraine episode is not met 212 and return to the selection step 208 to analyze another selected subset of data until all stored data has been analyzed.

If the system server 110 determines that a migraine episode threshold has been met for a particular user from the analysis of the selected subset of data, a migraine alert will be generated and sent to the user, provider medical professional, or caretaker 214.

EXAMPLES

Example 1

Migraine Associated Data Monitoring with an Ocular Device and Manual Data Input

A woman suffering from migraines wears an ocular device described herein. Upon sensing an oncoming migraine, she triggers the ocular device using the sensor pad, which signals to a plurality of sensors, found on the ocular device and in her smart watch, to take a measurement of data. The data recorded from the sensors includes the wavelengths of light, illuminance of light, humidity, barometric pressure, altitude, location, and heart rate of the woman at the moment she triggers the ocular device. The woman also manually records daily dietary data, medication taken, and number of hours of sleep every night. The woman continues to use the ocular device and collects data over a period of two months, during which she experiences several migraines. The collected data are kept on the computer readable storage media and prior to a meeting with her physician, she sorts the data to include only the raw data collected within 24 hours of each migraine occurrence which she then downloads and prints. She also creates a report summarizing correlations between occurrences of her migraines with the collected migraine associated data. The raw data shows that in 7 out of the 10 migraines experiences, red wine had been consumed the day before and in 9 out of the 10 migraines she had been experience a high illuminance of light corresponding to direct sunlight (32,000-100,000 lux); and these data correlate strongly with occurrence of migraines. She shares these data with her physician, who recommends that she both avoid red wine as well as program her optical device to automatically activate when light illuminance surpasses a specific threshold (32,000 lux).

Example 2

Migraine Associated Data Monitoring with an Ocular Device

A man suffering from migraines wears an ocular device described herein. Upon sensing an oncoming migraine, he triggers the ocular device using the sensor pad, signaling to a plurality of sensors on the ocular device to take a measurement of data. The data recorded from the sensors includes the wavelengths of light, illuminance of light, frequency of sound, and intensity of sound at the moment he triggers the ocular device. The man continues to use the ocular device and collects data over a period of six months, during which he experiences a sharp increase in the frequency of his migraines after the three month mark. The collected data are stored on the computer readable storage media. He then creates a report summarizing correlations between occurrences of his migraines with the collected migraine associated data. A strong correlation is shown between occurrence of his migraines and low frequency sound, below normal human perception (below 20 Hz). The man remembers a commercial wind farm had recently been build and completely about three months ago less than a mile away from his place of employment. He purchases a pair of noise canceling headphones to wear at work.

Example 3

Migraine Associated Data Monitoring with a FitBit

A 9-year old child suffering from migraines wears a FitBit Charge HR operatively connected to a non-transitory computer readable storage media of his mother's computing device. Daily baseline recordings are taken once a day at 8 am, regarding number of steps taken, amount and quality of sleep, and current heart rate. Additional measurements of migraine associated data are also taken when, upon realizing her child is suffering from a migraine, the mother of the child triggers the sensor. During their next pediatrician visit, the mother shares with the pediatrician, via the interface with her computing device, the results of the past two weeks of data collection. The pediatrician notices that during the two instances when the child experienced a migraine his heart rate increased significantly compared to baseline heart rate measurements. The mother then reprograms her computing device to take baseline measurements of her child's heartrate from once per day to twenty times per day in order to better monitor his heart rate, which may indicate he is about to experience a migraine, thus facilitating quicker intervention.

Example 4

Aggregate Migraine Associated Data Collection

Ten thousand individuals who suffer from migraines around the United States are using the ocular device coupled with a computer readable storage media to collect and monitor their personal migraine associated data. The individuals agree to share their data with a remote server for use in migraine research purposes. A group of migraine researchers accesses this wealth of data to look for correlations of increased migraine occurrence over the past two years with an increase in urbanization and air pollution. Using the location data collected for each individual, they are able to group individuals into relevant subpopulations and occurrences of migraines are monitored over time and in relation to fluctuating air pollution levels as obtained from the United States Environmental Protection Agency.

What is claimed is:
1. A platform for collecting migraine associated data for an individual who experiences migraines, comprising:
a) a sensor comprising:
 i) a detector used to automatically and instantaneously collect migraine associated environmental, physiological, and self-reported data; and
 ii) a communications element used to transmit migraine associated data collected by the detector to non-transitory computer readable storage media; and
b) a non-transitory computer readable storage media encoded with a computer program including instructions executable by a processor to create an application comprising:
 i) a software module used to receive the migraine associated data from the sensor; and
 ii) a software module used to present an interface allowing the user to interact with the migraine associated data;
c) a module applying an algorithm to said migraine associated data to generate analytic data correlating said migraine associated data with a migraine occurrence and/or comprising trends in such correlations;
d) an ocular device comprising:
 i) a first mode that allows a target light wavelength or a target light intensity to pass through the first lens;
 ii) a second mode that reduces or substantially blocks the target light wavelength or the target light intensity from passing through the first lens;
 iii) a voltage source operatively coupled to the first lens and configured to generate a voltage, wherein application of the voltage to the first lens switches the first lens from the first mode to the second mode; and
 iv) an activator operatively coupled to the voltage source, and configured to activate the voltage source upon receipt of a signal from a signal receiver;

v) wherein the target light wavelength or the target light intensity is associated with an occurrence of migraine headaches in the individual;

e) transmitting a notification when migraine associated data is above a specific threshold or within a specific range and presenting said notification in a report.

2. The platform of claim 1, wherein the sensor is physically coupled to the ocular device.

3. The platform of claim 1, wherein the platform comprises a plurality of sensors.

4. The platform of claim 1, wherein the migraine associated data comprises environmental data.

5. The platform of claim 1, wherein the sensor records a baseline measurement of the migraine associated data.

6. The platform of claim 1, wherein the sensor is located in a mobile device, a smart phone, a smart watch, a wearable device, or a combination thereof.

7. The platform of claim 1, wherein the measurement of migraine associated data is taken when the sensor is triggered automatically.

8. The platform of claim 1, wherein the measurement of migraine associated data is taken when the sensor is triggered manually.

9. A method of recording migraine associated data for an individual who experiences migraines comprising the steps of:
   a) receiving a sensor operatively connected to a non-transitory computer readable storage media; and
   b) instructing of the non-transitory computer readable storage media to signal the sensor to automatically and instantaneously make a measurement of the migraine associated environmental, physiological, and self-reported data, wherein making a measurement of the migraine associated data comprises:
      i) recording of the migraine associated data by the sensor;
      ii) transmitting the migraine associated data from the sensor to the non-transitory computer readable storage media; and
      iii) storing the migraine associated data on a memory of the non-transitory computer readable storage media
   c) applying an algorithm to said migraine associated data to generate analytic data correlating said migraine associated data with a migraine occurrence and/or comprising trends in such correlations;
   d) receiving an ocular device comprising:
      i) a first mode that allows a target light wavelength or a target light intensity to pass through the first lens;
      ii) a second mode that reduces or substantially blocks the target light wavelength or the target light intensity from passing through the first lens;
      iii) a voltage source operatively coupled to the first lens and configured to generate a voltage, wherein application of the voltage to the first lens switches the first lens from the first mode to the second mode; and
      iv) an activator operatively coupled to the voltage source, and configured to activate the voltage source upon receipt of a signal from a signal receiver;
      v) wherein the target light wavelength or the target light intensity is associated with an occurrence of migraine headaches in the individual;
   e) transmitting a notification when migraine associated data is above a specific threshold or within a specific range and presenting said notification in a report.

10. The method of claim 9, wherein the sensor is physically coupled to the ocular device.

11. The method of claim 9, wherein the sensor records a baseline measurement of the migraine associated data.

12. The method of claim 9, wherein the migraine associated data comprises environmental data, physiological data, self-reported data, or a combination thereof.

13. The method of any of the preceding claims, wherein the sensor is located in a mobile device.

14. The method of claim 9 wherein the measurement of migraine associated data is taken when the sensor is triggered automatically.

15. The method of claim 9, wherein the measurement of migraine associated data is taken when the sensor is triggered manually.

16. The method of claim 9, further comprising generating a report of the migraine associated data.

17. The method of claim 9, further comprising transmitting the recorded migraine associated data from the memory of the non-transitory computer readable storage media to a server.

18. The method of claim 17, wherein migraine associated data from a plurality of individuals is aggregated on the server.

* * * * *